US00PP16753P3

(12) United States Plant Patent
Ligonniere

(10) Patent No.: US PP16,753 P3
(45) Date of Patent: Jul. 4, 2006

(54) APPLE TREE NAMED 'DALITRON'

(50) Latin Name: *Malus domestica*
Varietal Denomination: Dalitron

(75) Inventor: Guy Raymond Ligonniere, Angers (FR)

(73) Assignee: SNC Elaris, Angers (FR)

( * ) Notice: Subject to any disclaimer, the term of this patent is extended or adjusted under 35 U.S.C. 154(b) by 61 days.

(21) Appl. No.: 10/940,284

(22) Filed: Sep. 13, 2004

(65) Prior Publication Data

US 2005/0076414 P1 Apr. 7, 2005

(51) Int. Cl.
*A01H 5/00* (2006.01)

(52) U.S. Cl. ..... Plt./161
(58) Field of Classification Search ..... Plt./161
See application file for complete search history.

(56) References Cited

U.S. PATENT DOCUMENTS

2005/0076414 P1 * 4/2005 Ligonniere ..... Plt./161

OTHER PUBLICATIONS

UPOV ROM GTITM Computer Database, GTI JOUVE Retrieval Software 2005/03, Citation for 'Dalitron'.*

* cited by examiner

*Primary Examiner*—Kent Bell
*Assistant Examiner*—W. C. Haas
(74) *Attorney, Agent, or Firm*—Stratton Ballew PLLC

(57) ABSTRACT

A new apple tree named 'Dalitron' is disclosed. The fruit of the new variety is particularly notable for its eating quality and distinctive appearance. The fruit is firm, crunchy, juicy and fully flavored, and takes on a distinctive solid bright yellow coloration during storage. 'Dalitron' apples maintain favorable texture and firmness during and after long term storage.

7 Drawing Sheets

Latin name of the genus and species of the plant claimed: *Malus domestica.*
Variety denomination: 'Dalitron'.

BRIEF DESCRIPTION OF THE VARIETY

'Dalitron' originated from a controlled cross of seed parent 'Golden Delicious' (unpatented) and pollen parent 'Pilot' (not patented; French Plant Variety Rights Certificate No. 7471) at Moulin Neuf, Lezigne, France in 1994. The seedling was selected as a single plant from among eighty-five (85) seedlings resulting from the cross, and planted in a test orchard in 1997 for evaluation. 'Dalitron' was first asexually propagated in 2000 at Moulin Neuf, and has been shown to reproduce true to type through successive generations.

'Dalitron' is distinguishable from its seed parent 'Golden Delicious' by its upright habit, early flowering (two days earlier than 'Golden Delicious'), large, abundant leaves and flowers, bright yellow fruit coloration, and improved fruit storageability.

'Dalitron' is distinguishable from its pollen parent 'Pilot' by its large leaves and flowers, later flowering (five days after 'Pilot'), and distinctive truncate-conical fruit shape.

BRIEF DESCRIPTION OF THE PHOTOGRAPHS

DETAILED BOTANICAL DESCRIPTION OF THE VARIETY

Figure 1:
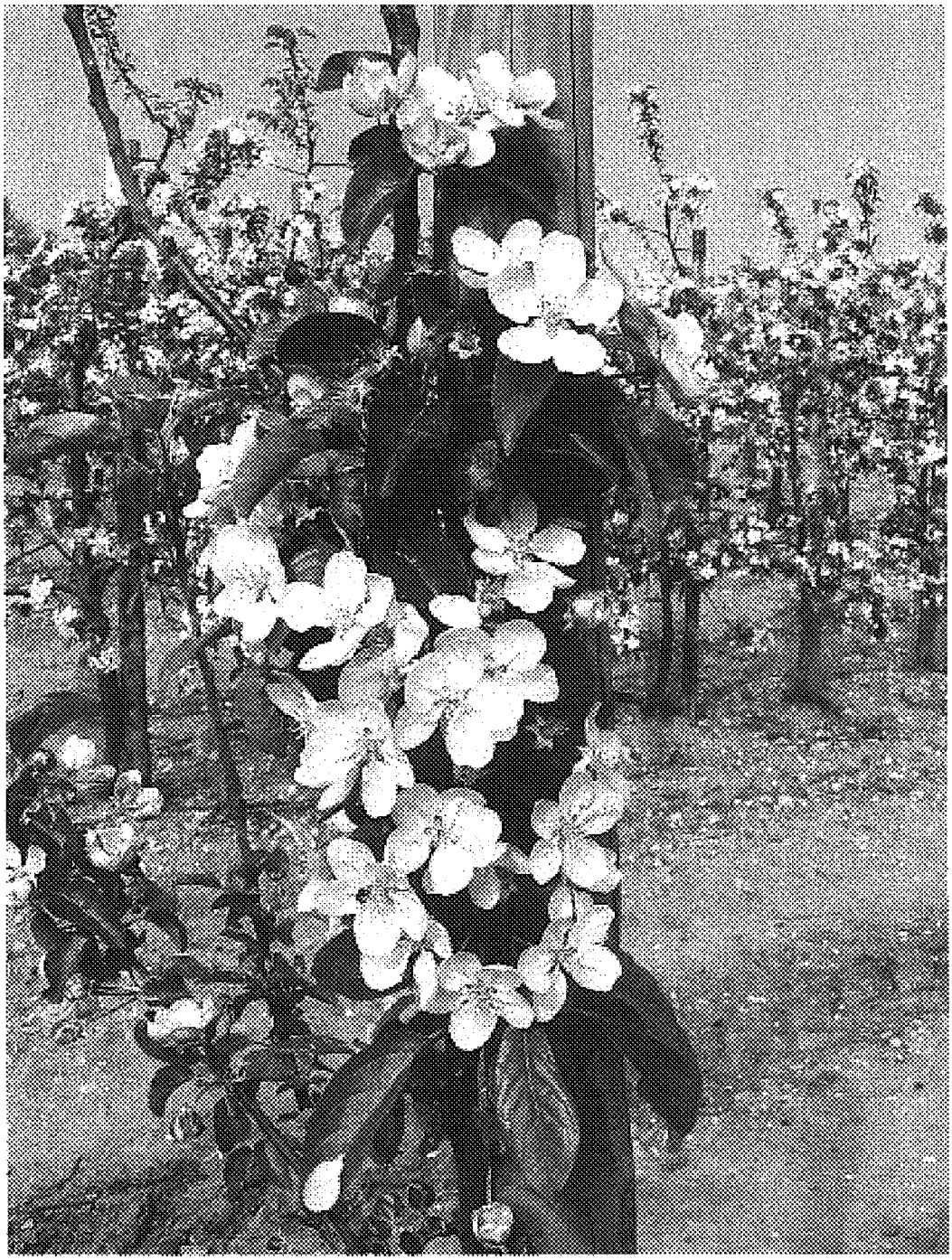
FIG. 1 shows the blossoms and leaves of the claimed variety.
Figure 2:
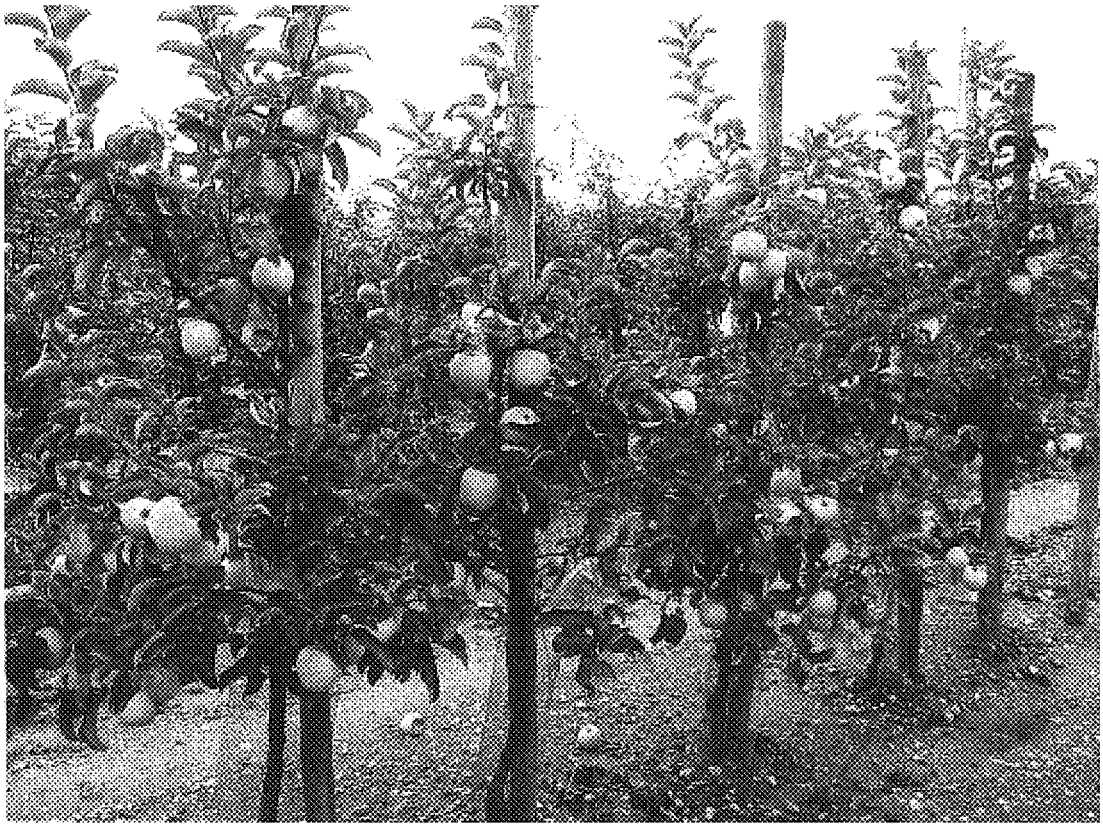
FIG. 2 shows two-year-old trees of the claimed variety.
Figure 3:
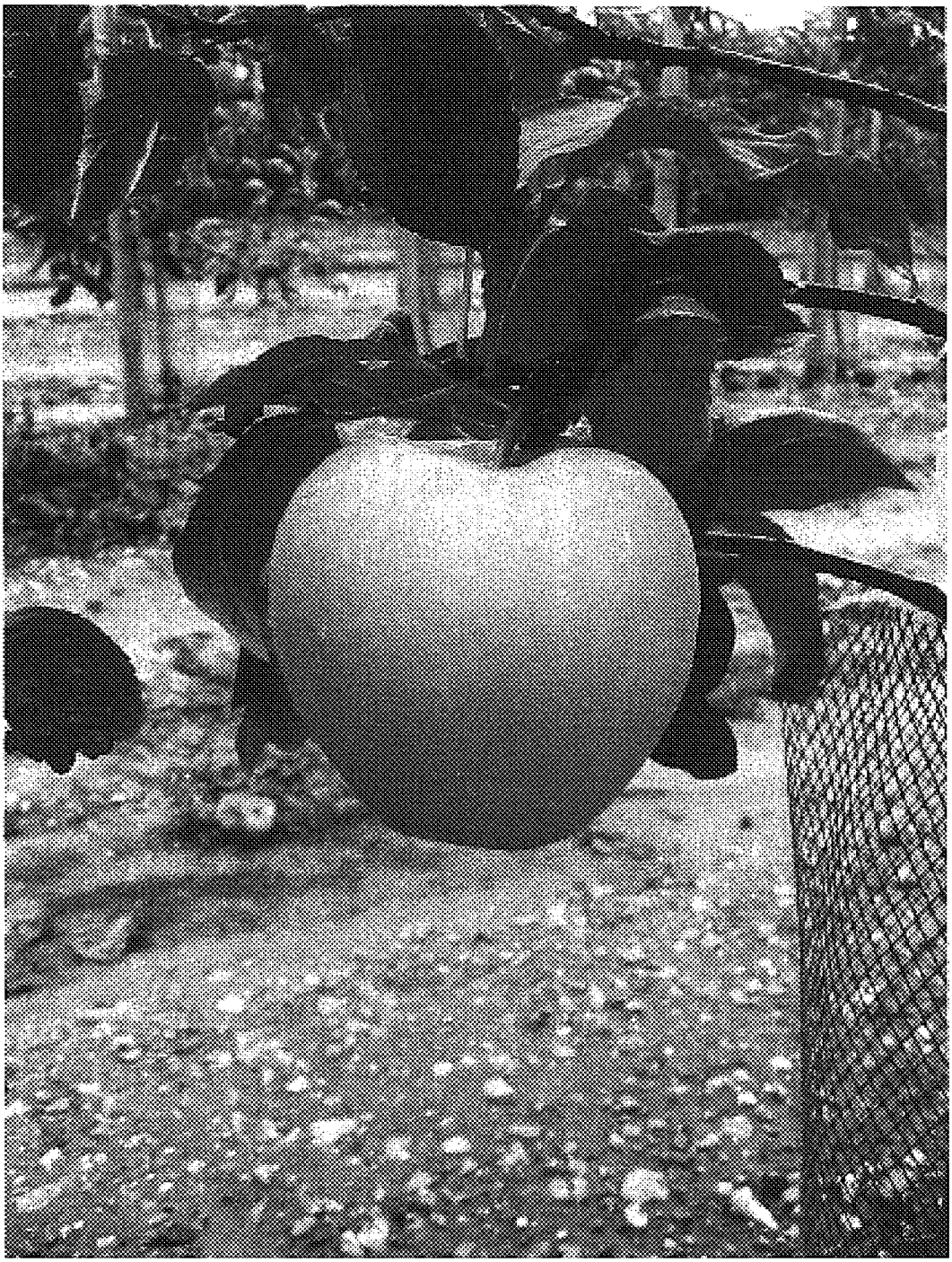
FIG. 3 shows the fruit and leaves of the claimed variety.
Figure 4:
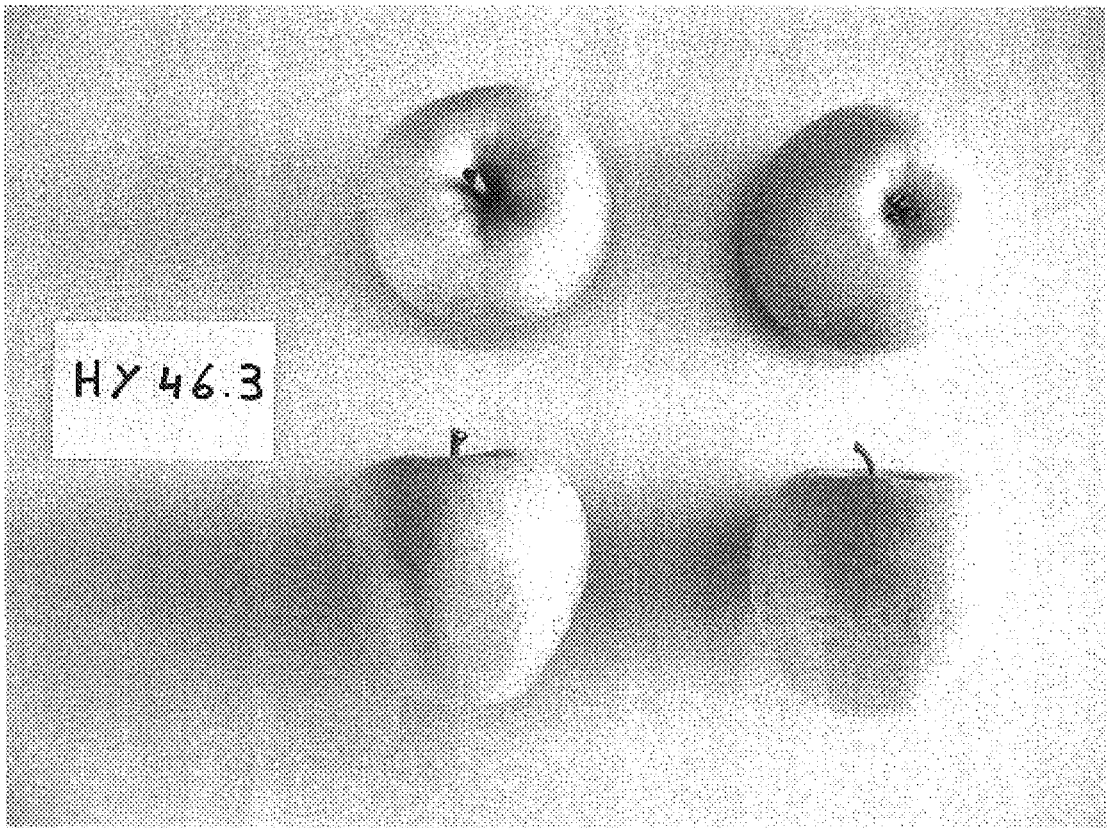
FIG. 4 shows the fruit of the claimed variety after four (4) months in storage.
Figure 5:
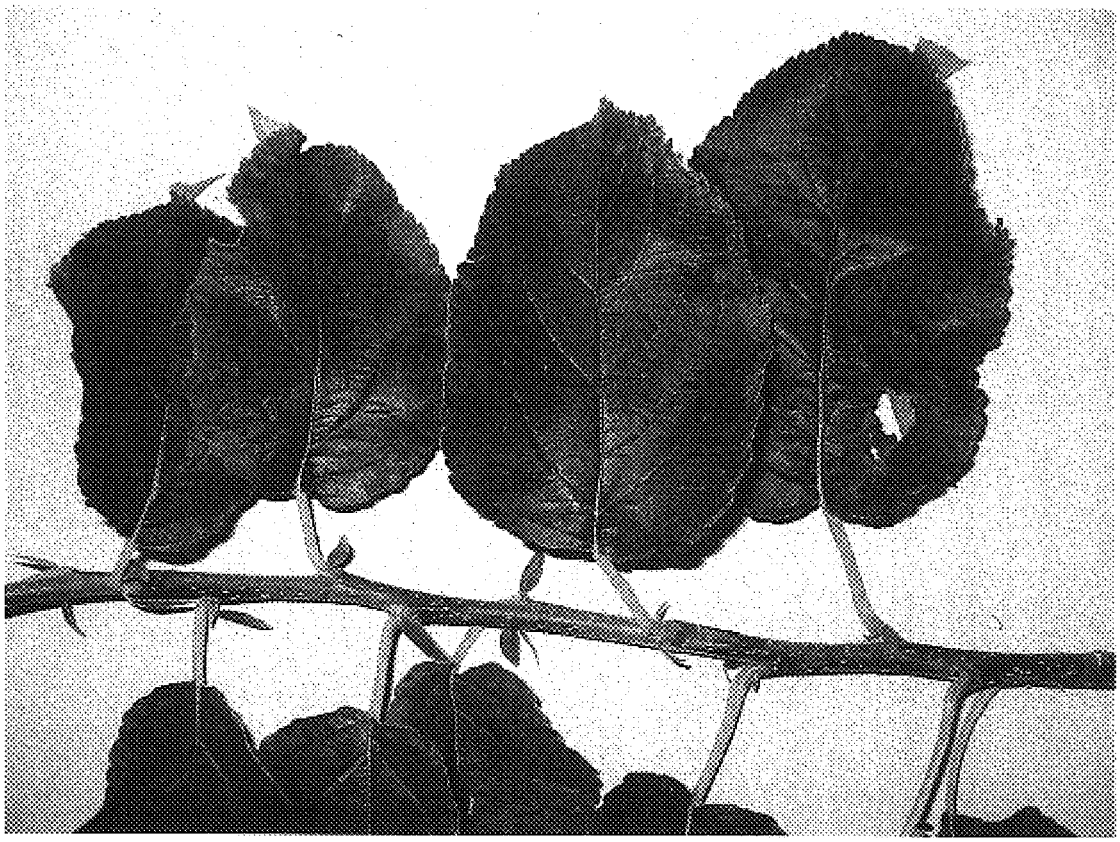
FIG. 5 shows the leaves of the claimed variety on a one-year-old shoot.
Figure 6:
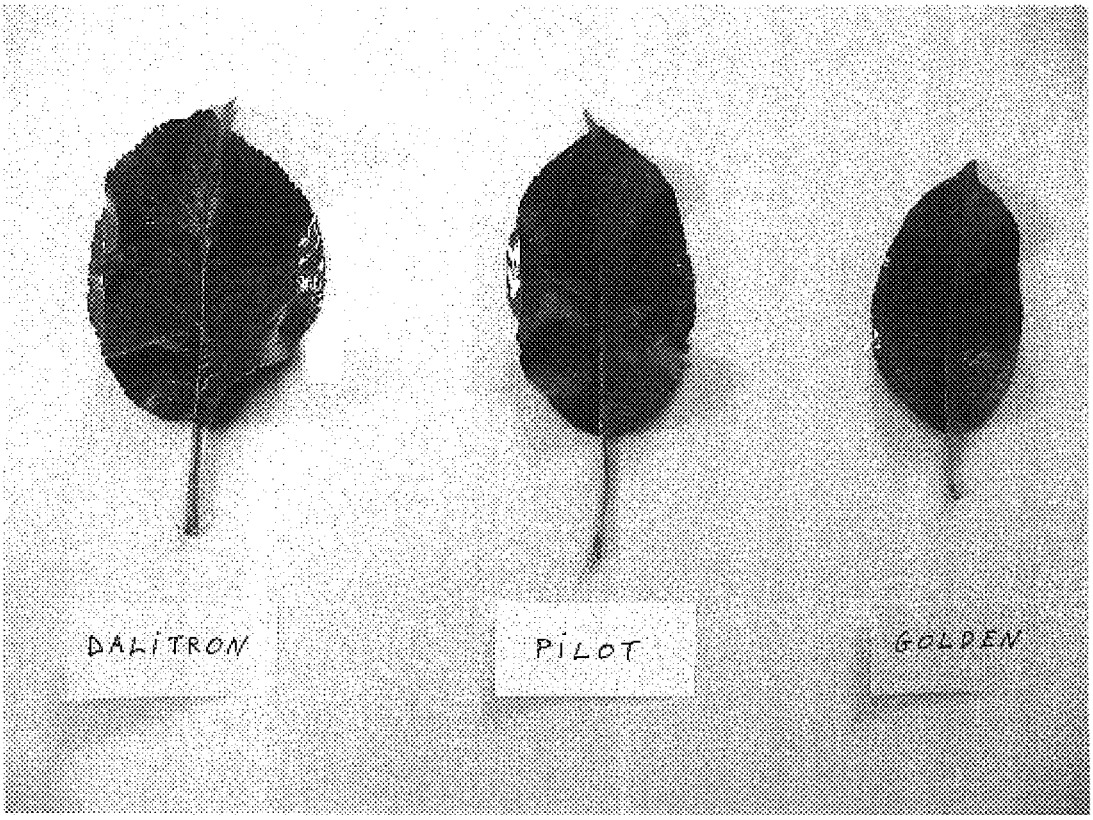
FIG. 6 shows the leaves of 'Dalitron' as compared to its parents.
Figure 7:
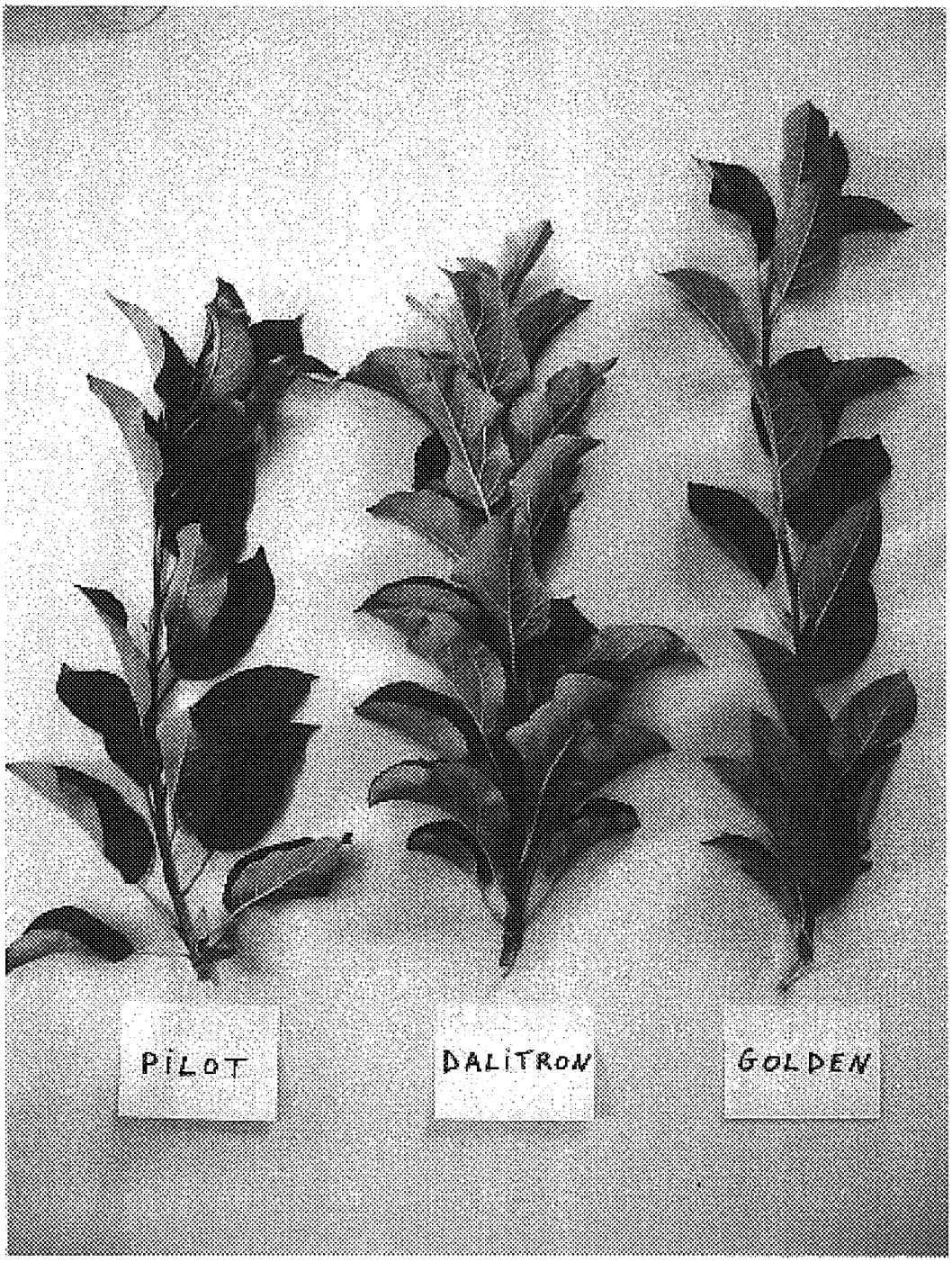
FIG. 7 shows a one-year-old shoot of 'Dalitron' as compared to its parents.

The following is a detailed botanical description of 'Dalitron,' based on observations of the seven year old mother tree planted in 1998, and 14 first generation trees planted in 2002, in Moulin Neuf, Lezigne, France. Colors, except those colors described in common terms, are set forth in accordance with The Royal Horticultural Society Colour Chart. The botanical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

1. Tree (measurements on 3 year old trees on 'M9' rootstocks (not patented) in high density planting):
   *Vigor.*—Quite strong (stronger than 'Golden Delicious').
   *Type.*—Columnar to ramified (for less ramifications than 'Golden Delicious').

*Habit.*—Upright-spreading.

*Size.*—Height, 2.3 m; diameter, 1.3 m.

*Trunk.*—Diameter 29 mm at 30 cm above graft union; bark texture medium; color grey-brown N199B.

*Branches.*—Fruiting branches located at around 1 m above the graft union: Quite long, 96 cm; diameter large, 11.7 mm; crotch angle 60° to 80°; color brown 200B.

*Winter hardiness.*—Similar to 'Golden Delicious'.

*Chilling requirement.*—Similar to 'Golden Delicious'.

2. Dormant one year old shoot:

*Pubescence.*—Medium to strong.

*Size.*—Thick, 6 mm (compare to 'Pilot' 5 mm and 'Golden Delicious' 4.5 mm).

*Color.*—Green 143B.

*Internode length.*—Quite short, 2.1 cm (compare to 'Pilot' 2.4 cm and 'Golden Delicious'2.9 cm).

*Number of lenticels.*—Medium, 8 per $cm^2$.

3. Flowers:

*Bud.*—Quantity per spur 2 to 3; round to conical; length 1.4 cm; diameter 1.7 cm; color red-purple 61A.

*Flower color (balloon stage).*—Purple 77B.

*Size.*—Very large, diameter 4.7 mm; quite deep, 1.7 cm; quantity per cluster usually 5, sometimes 4.

*Petals.*—Quantity per flower 5; margins smooth, slightly touching or sometimes free; length 2.7 cm; width 1.7 cm; apex round; base conical-pointed; upper surface color white N155B; lower surface color white N155B to purple N78C when fully open.

*Reproductive organs.*—Pistils quite long, 1.4 cm, color yellow-green 144C; Anthers numerous, avg. 12 per flower, length 2.5 mm, pollen color yellow 4B; Stigma small to medium, 0.5 mm, color yellow-green 150B; Style long, 1.2 cm; yellow-green N144D; Ovary medium size, 0.2 cm, color green 134A.

*Bloom period.*—First bloom April 10 at Angers (2 days before 'Golden Delicious'); full bloom April 15 at Angers (2 days before 'Golden Delicious').

*Pedicel.*—Long, 2.9 cm; thin, 1.4 mm; color green 143B.

*Sepals.*—5 per flower; conical-pointed; color green 143C.

4. Leaf: Attitude in relation to shoot Markedly upwards.

5. Leaf blade:

*Length.*—Long, 11.1 cm.

*Width.*—Wide, 7.4 cm.

*Length-width ratio.*—Medium.

*Margin.*—Serrate.

*Shape.*—Ovate to oval; apex acuminate; base oblique.

*Color.*—Upper surface green 137A; lower surface 138B.

TABLE 1

Comparison to of 'Dalitron' leaves to 'Golden Delicious' and 'Pilot'

| | 'Dalitron' | 'Golden Delicious' | 'Pilot' |
|---|---|---|---|
| Internode length | 2.1 cm | 2.9 cm | 2.4 cm |
| Leaf length | 11.1 cm | 9.4 cm | 10.5 cm |
| Leaf width | 7.4 cm | 5.6 cm | 6.4 cm |
| Length/width ratio | 1.5 cm | 1.7 cm | 1.6 cm |

6. Petiole: Length medium, 2.7 cm; diameter thick, 2.9 mm; color yellow-green 145B.

7. Fruit:

*Size.*—Large; 236 g; diameter 78 mm; height 79 mm.

*Ratio of height to width.*—Medium.

*General shape in profile.*—Truncate conical, round to elongated.

*Position of maximum diameter.*—Top third of the fruit, close to the stem bowl.

*Ribbing.*—Absent to very weak.

*Crowning at calyx end.*—Very weak.

*Aperture of eye.*—Closed.

*Size of eye.*—Large, 1 cm.

*Eye basin.*—Depth, 13 mm; width, 3.4 cm.

*Stalk.*—Diameter thin, 2.1 mm; length 2.9 cm; color brown 200D.

*Depth of stalk cavity.*—Quite deep, 14 mm.

*Width of stalk cavity.*—Large, 44 mm.

*Size of lenticels.*—Very small, 0.5 mm.

*Bloom of skin.*—None.

*Greasiness of skin.*—Medium to strong.

*Ground color of skin.*—At harvest, green 142B; after storage, green-yellow 149B.

*Over color of skin.*—At harvest, green-yellow 150C; after storage, yellow 2B.

*Amount of over color.*—50%, becoming close to 100% after storage.

*Intensity of over color.*—Bright.

*Pattern of over color.*—Only solid flush.

*Flesh.*—Texture medium to fine; quite juicy; color 155D; 14° Brix at harvest time.

*Seeds.*—Quantity per fruit 9; truncate ovoid; color brown 200C.

*Quantity per cluster.*—3 to 4.

*Aroma.*—Complex aroma, including banana and exotic fruit flavors.

*Yield.*—40 fruits in second leaf; 70 fruits in third leaf.

*Use.*—Fresh market.

*Resistance to known diseases.*—None noted.

*Storageability.*—Good (better than 'Golden Delicious,' similar to 'Pilot').

I claim:

1. A new and distinct apple tree as described and illustrated herein.

* * * * *

UNITED STATES PATENT AND TRADEMARK OFFICE

CERTIFICATE OF CORRECTION

PATENT NO. : PP 16,753 P3
APPLICATION NO. : 10/940284
DATED : July 4, 2006
INVENTOR(S) : Guy Raymond Ligonniere It is certified that error appears in the above-identified patent and that said Letters Patent is hereby corrected as shown below:

Column 2,
Line 32, "for" should read --far--.

Signed and Sealed this

Seventh Day of November, 2006

JON W. DUDAS
*Director of the United States Patent and Trademark Office*